United States Patent [19]

Yuh et al.

[11] Patent Number: 5,028,502

[45] Date of Patent: Jul. 2, 1991

[54] HIGH SPEED ELECTROPHOTOGRAPHIC IMAGING SYSTEM

[75] Inventors: Huoy-Jen Yuh, Pittsford; Damodar M. Pai, Fairport; John F. Yanus, Webster, all of N.Y.

[73] Assignee: Xerox Corporation, Stamford, Conn.

[21] Appl. No.: 471,769

[22] Filed: Jan. 29, 1990

[51] Int. Cl.$^5$ ............................................. G03G 13/22
[52] U.S. Cl. ......................................... 430/31; 430/59
[58] Field of Search ................................... 430/31, 59

[56] References Cited

U.S. PATENT DOCUMENTS

| | | |
|---|---|---|
| 3,620,729 | 11/1971 | Ray-Chaudhuri et al. |
| 3,881,925 | 5/1975 | Uchida et al. |
| 3,997,342 | 12/1976 | Bailey |
| 4,025,341 | 5/1977 | Rule |
| 4,066,455 | 1/1978 | Mey et al. |
| 4,081,274 | 3/1978 | Horgan |
| 4,092,162 | 5/1978 | Wright et al. |
| 4,150,987 | 4/1979 | Anderson et al. |
| 4,175,960 | 11/1979 | Berwick et al. ............ 430/58 |
| 4,209,579 | 6/1980 | Pu et al. ..................... 430/78 |
| 4,265,990 | 5/1981 | Stolka et al. ............... 430/59 |
| 4,284,698 | 8/1981 | Kazami et al. ............. 430/59 |
| 4,299,897 | 10/1981 | Stolka et al. ............... 430/59 |
| 4,471,039 | 9/1984 | Borsenberger et al. .... 430/58 |
| 4,487,824 | 12/1984 | Katagiri et al. ............ 430/58 |
| 4,504,564 | 3/1985 | Pai et al. .................... 430/132 |
| 4,515,882 | 5/1985 | Mammino et al. ......... 430/58 |
| 4,533,232 | 8/1985 | Fujimura et al. .......... 430/60 |
| 4,578,334 | 3/1986 | Borsenberger et al. .... 430/59 |
| 4,619,880 | 10/1986 | Horie et al. ................ 430/58 |
| 4,650,737 | 3/1987 | Wiedemann ............... 430/59 |
| 4,663,259 | 5/1987 | Fujimura et al. .......... 430/58 |
| 4,666,809 | 5/1987 | Matsumoto et al. ....... 430/76 |
| 4,701,396 | 10/1987 | Hung et al. ................ 430/58 |
| 4,719,163 | 1/1988 | Staudenmayer et al. ... 430/58 |
| 4,761,359 | 8/1988 | Sakai et al. ................ 430/31 X |
| 4,800,145 | 1/1989 | Nelson et al. .............. 430/58 |
| 4,833,054 | 5/1989 | Akasaki et al. ............ 430/59 |

*Primary Examiner*—Roland Martin

[57] ABSTRACT

An electrophotographic imaging process including providing an electrophotographic imaging member containing a change generating layer and a charge transport layer, the charge transport layer containing polystyrene film forming binder and certain specified aromatic diamine or certain specified hydrazone charge transport molecules, depositing a uniform electrostatic charge on the imaging member with a corona charging device, exposing the imaging member to activating radiation in image configuration to form an electrostatic latent image on the imaging member, developing the electrostatic latent image with electrostatically attractable marking particles to form a toner image, transferring the toner image to a receiving member and repeating the depositing, exposing, developing and transferring steps, the time elapsed between the exposing and the developing steps being between about 0.5 millisecond and about 500 milliseconds.

12 Claims, 1 Drawing Sheet

HIGH SPEED ELECTROPHOTOGRAPHIC IMAGING SYSTEM

This invention relates in general to electrophotographic imaging members and more specifically, to high speed electrophotographic imaging systems utilizing imaging members having a charge transport layer.

In the art of electrophotography an electrophotographic plate comprising a photoconductive insulating layer on a conductive layer is imaged by first uniformly electrostatically charging the imaging surface of the photoconductive insulating layer. The plate or photoreceptor is then exposed to a pattern of activating electromagnetic radiation such as light, which selectively dissipates the charge in the illuminated areas of the photoconductive insulating layer while leaving behind an electrostatic latent image in the non-illuminated area. This electrostatic latent image may then be developed to form a visible image by depositing finely divided electroscopic toner particles on the surface of the photoconductive insulating layer. The resulting visible toner image can be transferred to a suitable receiving member such as paper. This imaging process may be repeated many times with reusable photoconductive insulating layers. The plate or photoreceptor can also be imaged utilizing a dark area discharge scheme. In this process, the charged device is exposed by a laser source which selectively discharges the dark areas of the original document. Development in this scheme involves toner particles adhering to the discharged areas of the image. The resulting toner image is subsequently transferred to a suitable receiving member such as paper.

One common type of photoreceptor is multilayered device that comprises a conductive layer, a charge generating layer, and a charge transport layer. Either the charge generating layer or the charge transport layer may be located adjacent the conductive layer. The charge transport layer can contain an active aromatic diamine small molecule charge transport compound dissolved or molecularly dispersed in an inactive film forming binder. This type of charge transport layer is described, for example in U.S. Pat. No. 4,265,990. Although excellent toner images may be obtained with such multilayered photoreceptors, it has been found that a plateau is reached when attempts are made to increase charge carrier mobility in the charge transport layer, particularly when the charge transport layer is fabricated by dip coating. Charge carrier mobilities determine the velocities at which the photoinjected carriers transit the transport layer. To achieve maximum discharge or sensitivity for a fixed exposure, the photoinjected carriers must transit the transport layer before the imagewise exposed region of the photoreceptor arrives at the development station. To the extent the carriers are still in transit when the exposed segment of the photoreceptor arrives at the development station, the discharge is reduced and hence the contrast potentials available for development are also reduced. For greater charge carrier mobility capabilities, it is normally necessary to increase the concentration of the active small molecule transport compound dissolved or molecularly dispersed in the binder. Generally, active small molecule transport compounds do not dissolve or molecularly disperse well in most inactive film forming polymeric binders. For example, less than 10 percent by weight of active aromatic diamine small molecule charge transport compounds can be dissolved or molecularly dispersed in phenoxy resins. Although higher concentrations of active aromatic diamine small molecule charge transport compounds may be achieved with polycarbonate resins, the active small molecule charge transport compound tends to crystallize as the concentration of the active small molecule transport compound is increased in the binder, particularly when applied as a solution by dip coating techniques. The limit to the maximum concentration of the small molecule is set by the onset of crystallization in the transport layer. This molecular concentration limit before the onset of crystallization, is found to be dependent on the fabrication process. Thus, in order to apply charge transport layers to photoreceptors by dip coating and avoid exceeding the maximum concentration limit set by onset of crystallization in the transport layer, lower concentrations of small molecule transport compounds must be used and this lower concentration tends to reduce charge carrier mobility in the charge transport layer of multilayered photoreceptors. Lower charge carrier mobility reduces the processing speed of electrophotographic copiers, duplicators and printers.

Thus, in automatic imaging systems utilizing multilayered photoreceptors, there are deficiencies that limit electrophotographic processing speed. This affects the practical value of multilayered photoreceptors for high speed automatic electrophotographic copiers, duplicators and printers.

INFORMATION DISCLOSURES STATEMENT

U.S. Pat. No. 4,081,274, issued to Horgan on Mar. 28, 1978—An imaging member is disclosed comprising a first layer of electrically active charge transport material on a supporting substrate, a photoconductive layer overlying the charge transport layer and a second layer of charge transport material overlying the photoconductive layer, the photoconductive layer exhibiting the capability of photogeneration of charge carriers and injection of the charge carriers, one of the electrically active layers comprising an electrically inactive resinous material made electrically active by the addition of certain activating compounds thereto. One of the activating compounds useful as an additive to the electrically inactive polymeric material making it electrically active is N,N'-diphenyl-N,N'-bis(phenylmethyl)-[1,1'-biphenyl]-4,4'-diamine. Another compound useful as an additive to the electrically inactive polymeric material making it electrically active is another aromatic amine illustrated, for example, in column 4, line 9 through column 5, line 26. Still another aromatic diamine compound which may be added to the electrically inactive polymeric material to render it electrically active is described in column 5, line 46 through column 6, line 2. These aromatic diamines are also further discussed in column 9, line 31 through column 12, line 33.

U.S. Pat. No. 4,265,990, issued to Stolka et al. on May 5, 1981—A photosensitive member is disclosed having photoconductive layer and a charge transport layer, the charge transport layer containing an aromatic diamine.

U.S. Pat. No. 4,299,897, issued to Stolka et al. on Nov. 10, 1981—A photosensitive member is disclosed having two electrically operative layers, the first layer comprising a photoconductive layer and the second layer comprising a contiguous charge transport layer. The charge transport layer comprises an electrically inactive organic resinous material and various aromatic diamines such as N,N,N',N'-tetra-(4-methylphenyl-[2,2'-dimethyl-1,1'-biphenyl]-4,4'-diamine or N,N'- diphenyl-N,N'-bis(4-methylphenyl)-[2,2'-dimethyl-1,1'-biphenyl]-4,4'-diamine.

U.S. Pat. No. 4,833,054, issued to Akasaki et al. on May 23, 1989—An electrophotographic photoreceptor is disclosed comprising an electrically conductive support having thereon a photosensitive layer composed of a charge generating layer and a charge transport layer, wherein the charge generating layer contains a bisazo compound and the charge transport layer contains a benzidine compound. The generic formula for the benzidine compound (an aromatic diamine) is illustrated, for example, in column 2, lines 41-58 and column 12, line 15 through column 26, line 15.

U.S. Pat. No. 4,504,564 issued to Pai et al. on Mar. 12, 1985—A process is disclosed for preparing an electrophotographic imaging member comprising providing a photoconductive layer and depositing thereon a solution of polycarbonate and substituted N,N'-diphenyl-N,N'-bis(alkylphenyl)-[1,1'-biphenyl]-4,4'-diamine in a halogenated hydrocarbon solvent and halogen-free organic solvent having a boiling point greater than the boiling point of the halogenated hydrocarbon solvent to provide a stable charge transport layer when the solvents are removed.

U.S. Pat. No. 4,150,987 issued to Anderson, et al. on Apr. 24, 1979—A process for electrophotographic reproduction and a layered electrophotographic plate having a conventional charge generation layer and a p-type hydrazone containing charge transport layer are disclosed in which the surface of the charge transport layer is selectively discharged by actinic radiation as a result of the migration through the transport layer of charges generated in the charge generation layer as a result of the actinic radiation and injected into the transport layer, the hydrazone being represented by a specific formula.

U.S. Pat. No. 4,471,039 issued to Borsenberger et al. on Sept. 11, 1984—Photoconductive elements are disclosed comprising a support, an indium phthalocyanine charge generation layer and a charge transport layer. A partial listing of representative materials which may be employed as binders in the charge generation layer and charge transport layer include binders such as styrene-butadiene copolymers, polyvinyl toluenestyrene copolymers, styrene-alkyd resins, nitrated polystyrene, polymethylstyrene, polycarbonate and numerous other binders. In addition, it is indicated in column 8 lines 19-33 that "In general, it is found that polymers containing aromatic or heterocyclic groups are most effective as the binder materials because these polymers, by virtue of their heterocyclic or aromatic groups, tend to provide little or no interference with the transport of charge carriers through the layer." This implies that the transport is independent of binder be it polycarbonate or polystyrene.

U.S. Pat. No. 4,066,455 issued to Mey et al. on Jan. 3, 1978—A multiactive photoconductive element is disclosed having at least three layers and electrical contact with one another. The layers comprise a photoconductive selenium-containing layer, a charge-generation layer and an organic photoconductive-containing charge transport layer. A partial listing of representative materials which may be employed as binders in the charge-transport layers include styrene-butadiene copolymers, polyvinyl toluenestyrene copolymers, styrene-alkyd resins, nitrated polystyrene, polymethylstyrene, polycarbonate and numerous other binders. In addition, it is indicated in column 8 lines 45-59 that "In general, it is found that polymers containing aromatic or heterocyclic groups are most effective as the binder materials because these polymers, by virtue of their heterocyclic or aromatic groups, tend to provide little or no interference with the transport of charge carriers through the layer." This implies that the transport is independent of binder be it polycarbonate or polystyrene.

U.S. Pat. No. 4,175,960 issued to Berwick et al. on Nov. 27, 1979—A multi-active photoconductive insulating element is disclosed having at least two layers comprising a charge-generation layer and an organic photoconductive-containing charge-transport layer. A partial listing of representative materials which may be employed as binders in the charge-transport layer include binders such as styrene-butadiene copolymers, polyvinyl toluenestyrene copolymers, styrene-alkyd resins, nitrated polystyrene, polymethylstyrene, polycarbonate and numerous other binders. In addition, it is indicated in column 16 lines 40-54 that "In general, it is found that polymers containing aromatic or heterocyclic groups are most effective as the binder materials for use in the charge transport layers because these polymers, by virtue of their heterocyclic or aromatic groups, tend to provide little or no interference with the transport of charge carriers through the layer." This implies that the transport is independent of binder be it polycarbonate or polystyrene.

U.S. Pat. No. 4,578,334 issued to Borsenberger et al. on Mar. 25, 1986—A multi-active photoconductive insulating element is disclosed comprising a charge-generation layer and a charge transport layer. The charge-generating agent within the charge-generation layer comprises certain crystalline forms of a perylene compound. A partial listing of representative materials which may be employed as binders in the charge-transport layer include styrene-butadiene copolymers, polyvinyl toluenestyrene copolymers, styrene-alkyd resins, nitrated polystyrene, polymethylstyrene, polycarbonate and numerous other binders. In addition column 10 line 19-33 indicates that "In general, it is found that polymers containing aromatic or heterocyclic groups are most effective as the binder materials because these polymers, by virtue of their heterocyclic or aromatic groups, tend to provide little or no interference with the transport of charge carriers through the layer." This implies that the transport is independent of binder be it polycarbonate or polystyrene.

U.S. Pat. No. 4,701,396 issued to Hung et al. on Oct. 20, 1987—Photoconductive elements are disclosed which are made from fluorine-substituted titanylphthalocyanine pigments. Binders which may be employed in the charge generating layer and charge transport layer include styrene-butadiene coopolymers, polyvinyl toluenestyrene copolymers, styrene-alkyd resins, nitrated polystyrene, polyethylstyrene, polycarbonate and numerous other binders.

U.S. Pat. No. 4,719,163 issued to Staudemayer et al. on Jan. 12, 1988—A multi-active photoconductive insulating element is disclosed comprising a charge-generation layer and a charge-transport layer. The charge-generating agent in the charge-generating layer is a specific perylene compound. A partial listing of representative materials which may be used as binder in the charge-transport layer include styrene-butadiene copolymers, polyvinyl toluenestyrene copolymers, styrene-alkyd resins, nitrated polystyrene, polymethylstyrene, polycarbonate and numerous other binders. In addition column 9, lines 50-64 indicates that "In general, it is found that polymers containing aromatic or heterocyclic groups are most effective as the binder materials because these polymers, by virtue of their heterocyclic or aromatic groups, tend to provide little or no interference with the transport of charge carriers through the layer." This implies that the transport is independent of binder be it polycarbonate or polystyrene.

U.S. Pat. No. 4,092,162 issued to Wright el al. on May 3, 1978—A polymeric compound is disclosed having utility and multi-active photoconductive insulating elements. Such elements having at least two layers containing an aggregate photoconductive layer and electrical contact with a photoconductive-containing layer. A partial listing of representative materials may be employed as binders in the inorganic photoconductive-containing layer or organic photoconductive-containing layer include binders such as styrene-butadiene copolymers, polyvinyl toluenestyrene copolymers, styrene-alkyd resins, nitrated polystyrene, polymethylstyrene and numerous other binders.

U.S. Pat. No. 4,487,824 issued to Katagiri et al. on Dec. 11, 1984—An electrophotographic member is disclosed comprising an electrically conductive substrate and a layer containing a hydrazone compound. A charge transport layer can be formed by applying the hydrazone dissolved together with a binder. Examples of binders include copolymers such as styrene-butadiene copolymers, styreneacrylonitrile copolymer, and styrene-maleic acid copolymer. Various other binders are also disclosed.

U.S. Pat. No. 4,515,882 issued to Mammino et al. on May 7, 1985—An electrophotographic imaging member is disclosed comprising at least one photoconductive layer and an overcoating layer comprising a film forming continuous phase comprising charge transport molecules and finely divided charge injection enabling particles to disperse in the continuous phase. The continuous phase may contain a binder such as polystyrenes, polystyrene, styrene-alkyd resins and numerous other binders.

U.S. Pat. No. 4,284,698 issued to Kazami et al. on Aug. 18, 1981—A layer of electrophotographic photoconductor is disclosed comprising an electroconductive support, a photoconductive double layer consisting of a charge generation layer comprising a diazo pigment and a charge transport layer comprising a charge transport material capable of forming a charge transport complex by reaction of 2,4,7-trinitro-9-fluorenone. The charge transport material is dissolved in a solvent together with a resin such as polystyrene, styrene-butadiene copolymers and various other resins.

U.S. Pat. No. 3,881,925 issued to Uchida et al. on May 6, 1975—An electrophotographic material is disclosed comprising a zinc oxide type electrophotographic layer containing a binder of copolymerized acrylic resin. The electrophotographic layer may further contain low molecular polystyrene.

U.S. Pat. No. 3,620,729 issued to Somerset et al. on Nov. 16, 1971—A photoconductive coating composition for applications of substrates is disclosed, the resulting photoconductive coating comprising a layer of photoconductive pigment particles bonded to themselves and to the substrate with a styrene terpolymer.

U.S. Pat. No. 3,997,342 issued to Bailey on Dec. 14, 1976—A photoconductive element is disclosed having a charge-generation and a charge transport layer. The charged-generation layer comprises a finely divide cocrystalline complex and the charge transport layer contains an organic photoconductive charge transport material. Either or both of the layers also contain a protonic acid material. A partial listing of representative materials which may be employed as binders in the charge-transport layer include styrene-butadiene copolymers, polyvinyl toluenestyrene-copolymers, styrene-alkyd resins, nitrated polystyrene, polymethylstyrene and numerous other resins.

U.S. Pat. No. 4,025,341 issued to Rule on May 24, 1977—A photoconductive polymer, and photoconductive insulating compositions and elements containing the same are disclosed. The photoconductive polymer is a condensation product, preferably of low molecular weight tertiary aromatic amines and certain carbonyl-containing compounds. A partial listing of representative materials which may be employed as binders in the charge-transport layer include styrene-butadiene copolymers, polyvinyl toluenestyrene copolymers, styrene-alkyd resins, nitrated polystyrene, polymethylstyrene and numerous other resins.

U.S. Pat. No. 4,533,232 issued to Fujinura et al. on Aug. 6, 1985—An electrophotographic process is disclosed comprising charging an electrophotographic photosensitive member comprising a conductive substrate and a photosensitive layer which includes a charge generation layer and a charge transport layer containing a charge-transporting material; forming an image on the charged photographic photosensitive member by exposing the photosensitive member and developing the imaging with a developer. The binder resins for use in the charge transport layer include copolymers such as styrene-butadiene copolymers, styreneacrylonitrile copolymer, and styrene-maleic acid copolymer. Various other binders are also disclosed.

U.S. Pat. No. 4,209,579 issued to Pu et al. on June 24, 1980—An electrophotographic sensitive material is disclosed comprising an electrically conductive support, a photoconductive layer containing an organic photoconductive material containing in a dispersed state a quinocyanine pigment. The pigment is dispersed in a binder in single layers. Examples of binders listed include polystyrene, styrene-butadiene copolymers, styrene-methyl methacrylate copolymers and numerous other resins.

U.S. Pat. No. 4,619,880 issued to Horie et al. on Oct. 28, 1986—An integrated type electrophotographic light-sensitive material is disclosed comprising a charge generating layer and a charge transport layer, the charge generating layer containing a specific hydrazone compound. Binders which may be used in the charge generating layer or charge transport layer include polystyrene, styrene-butadiene copolymers, styrenealkyd resins, and various other binders.

U.S. Pat. No. 4,663,259 issued to Fujimura et al. on May 5, 1987—An electrophotographic photosensitive member is disclosed comprising a conductive substrate, a charge transport layer and a charge generating layer, the charge generating layer being superposed on the charge transport layer and the charge generating layer containing particles of a fluorine-containing resin. Examples of binders that may be employed in charge transport layer include styrene-butadiene copolymers, styreneacrylonitrile copolymers, styrene-maleic acid copolymers and various other binders.

U.S. Pat. No. 4,666,809 issued to Matsumoto et al. on May 19, 1987—An electrophotographic photosensitive member is disclosed having a conductive substrate and a photosensitive layer, the photosensitive layer comprising a binder and at least one hydrazone having a specific formula. The hydrazone compound may be used in a charge-transporting material. Examples of binders for the charge transport layer include styrene-butadiene copolymers, styrene-acrylonitrile copolymers, styrene-maleic acid copolymers and various other binders.

U.S. Pat. No. 4,800,145 issued to Nelson et al. on Jan. 24, 1989—An organic photoconductor is disclosed comprising an electrically conductive support, a charge generating phase comprising a charge generator and a charge transport phase characterizing that the charge generator is a specific phthalocyanine compound. Examples of resins for use in the charge transport phase include polystyrene, styrene-acrylic and various other resins.

U.S. Pat. No. 4,650,737 issued to Wiedemann on Mar. 17, 1987—A electrophotographic recording material is disclosed comprising an electrically conductive base, an optional insulating intermediate layer, and a photoconductive double layer comprising a charge-generating layer and a charge-transporting layer. The charge-transporting layer contains a benzimidazole transport compound, a binder and a dye or pigment. Binders include polystyrenes, copolymers of styrene with, for example, butadiene or acrylate esters, copolymers of styrene and maleic anhydride, copolymers of styrene, methacrylic acid and methacrylate ester, and numerous other binders are disclosed.

Thus there is a continuing need for electrophotographic imaging members having improved resistance to resolution loss and deletion, improved stability when exposed to ultraviolet radiation and continuing need for higher mobility values at low concentration of the active transport molecules.

SUMMARY OF THE INVENTION

It is, therefore, an object of the present invention to provide an improved electrophotographic imaging member which overcomes the above-noted disadvantages.

It is yet another object of the present invention to provide an electrophotographic imaging member exhibiting improved xerographic speeds.

It is still another object of the present invention to provide an electrophotographic imaging member exhibiting improved charge carrier mobilities at lower concentration of the transport molecules.

It is another object of the present invention to provide an electrophotographic imaging member possessing improved stability when exposed to ultraviolet radiation.

It is another object of the present invention to provide an electrophotographic imaging system for high speed imaging.

The foregoing objects and others are accomplished in accordance with this invention by providing an electrophotographic imaging process comprising providing an electrophotographic imaging member comprising a charge generating layer and a charge transport layer, the charge transport layer comprising polystyrene film forming binder and a charge transport molecule selected from the group consisting of an aromatic diamine represented by the general formula:

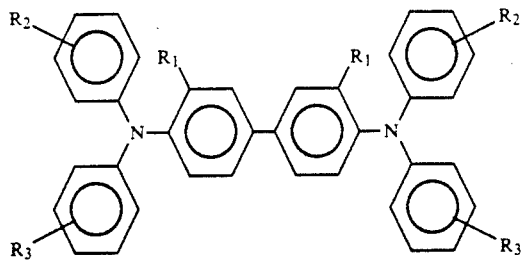

wherein $R_1$ represents hydrogen, an alkyl group or an alkoxy group, $R_2$ represents a hydrogen atom, an alkyl group, an alkoxy group, a halogen atom, an alkoxycarbonyl group or a substituted amino group and $R_3$ represents an alkyl group, an alkoxy group, a halogen atom, an alkoxycarbonyl group or a substituted amino group, and a hydrazone represented by the general formula:

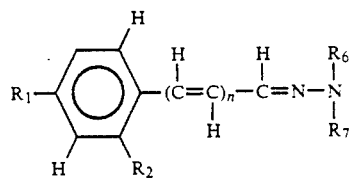

wherein
n=1,

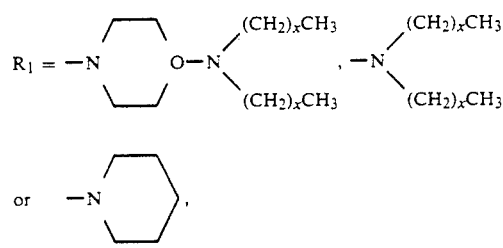

x=0, 1, 2, or 3,
$R_2 = -OCH_2CH_3$, $-CH_3$ or $-H$,

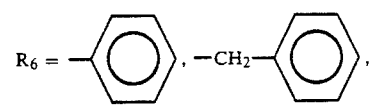

$-CH_3$ or $-CH_2CH_2CH_2CH_3$, and

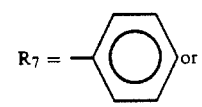

$-CH_3$, depositing a uniform electrostatic charge on the imaging member with a corona charging device, exposing the imaging member to activating radiation in image configuration to form an electrostatic latent image on the imaging member, developing the electrostatic latent image with electrostatically attractable marking particles to form a toner image. transfering the toner image to a receiving member and repeating the depositing, exposing, developing and transfering steps, the time elapsed between the exposing and the developing steps is between about 0.5 millisecond and about 500 milliseconds. These imaging members may be fabricated by dip coating techniques and used in high speed imaging apparatus.

Electrostatographic imaging members are well known in the art. Electrostatographic imaging member may be prepared by various suitable techniques. Typically, a flexible or rigid substrate is provided having an electrically conductive surface. A charge generating layer is then usually applied to the electrically conductive surface. An optional charge blocking layer may be applied to the electrically conductive surface prior to the application of the charge generating layer. If desired, an adhesive layer may be utilized between the charge blocking layer and the charge generating layer. Usually the charge generation layer is applied onto the blocking layer and a charge transport layer is formed on the charge generation layer. However, in some embodiments, the charge transport layer is applied prior to the charge generation layer.

The substrate may be opaque or substantially transparent and may comprise numerous suitable materials having the required mechanical properties. Accordingly, the substrate may comprise a layer of an electrically non-conductive or conductive material such as an inorganic or an organic composition. As electrically non-conducting materials there may be employed various resins known for this purpose including polyesters, polycarbonates, polyamides, polyurethanes, and the like. The electrically insulating or conductive substrate is preferably in the form of a rigid cylinder.

The thickness of the substrate layer depends on numerous factors, including strength and rigidity desired and economical considerations. Thus, this layer may be of substantial thickness, for example, about 5000 micrometers, or of minimum thickness of less than about 150 micrometers, provided there are no adverse effects on the final electrostatographic device. The surface of the substrate layer is preferably cleaned prior to coating to promote greater adhesion of the deposited coating. Cleaning may be effected, for example, by exposing the surface of the substrate layer to plasma discharge, ion bombardment and the like.

The conductive layer may vary in thickness over substantially wide ranges depending on the optical transparency and degree of flexibility desired for the electrostatographic member. Accordingly, for a photoresponsive imaging device having an electrically insulating, transparent cylinder, the thickness of the conductive layer may be between about 10 angstrom units to about 500 angstrom units, and more preferably from about 100 Angstrom units to about 200 angstrom units for an optimum combination of electrical conductivity and light transmission. The conductive layer may be an electrically conductive metal layer formed, for example, on the substrate by any suitable coating technique, such as a vacuum depositing technique. Typical metals include aluminum, zirconium, niobium, tantalum, vanadium and hafnium, titanium, nickel, stainless steel, chromium, tungsten, molybdenum, and the like. In general, a continuous metal film can be attained on a suitable substrate, e.g. a polyester web substrate such as Nylar available from E. I. du Pont de Nemours & Co. with magnetron sputtering.

If desired, an alloy of suitable metals may be deposited. Typical metal alloys may contain two or more metals such as zirconium, niobium, tantalum, vanadium and hafnium, titanium, nickel, stainless steel, chromium, tungsten, molybdenum, and the like, and mixtures thereof. Regardless of the technique employed to form the metal layer, a thin layer of metal oxide forms on the outer surface of most metals upon exposure to air. Thus, when other layers overlying the metal layer are characterized as "contiguous" layers, it is intended that these overlying contiguous layers may, in fact, contact a thin metal oxide layer that has formed on the outer surface of the oxidizable metal layer. Generally, for rear erase exposure, a conductive layer light transparency of at least about 15 percent is desirable. The conductive layer need not be limited to metals. Other examples of conductive layers may be combinations of materials such as conductive indium tin oxide as a transparent layer for light having a wavelength between about 4000 Angstroms and about 7000 Angstroms or a conductive carbon black dispersed in a plastic binder as an opaque conductive layer. A typical electrical conductivity for conductive layers for electrophotographic imaging members in slow speed copiers is about $10^2$ to $10^3$ ohms/square.

After formation of an electrically conductive surface, a hole blocking layer may be applied thereto for photoreceptors. Generally, electron blocking layers for positively charged photoreceptors allow holes from the imaging surface of the photoreceptor to migrate toward the conductive layer. For negatively charged photoreceptors the blocking layer allows electrons to migrate toward the conducting layer. Any suitable blocking layer capable of forming an electronic barrier to holes between the adjacent photoconductive layer and the underlying conductive layer may be utilized. The blocking layer may be nitrogen containing siloxanes or nitrogen containing titanium compounds such as trimethoxysilyl propylene diamine, hydrolyzed trimethoxysilyl propyl ethylene diamine, N-beta-(aminoethyl) gamma-amino-propyl trimethoxy silane, isopropyl 4-aminobenzene sulfonyl, di(dodecylbenzene sulfonyl) titanate, isopropyl di(4-aminobenzoyl)isostearoyl titanate, isopropyl tri(N-ethylamino-ethylamino)titanate, isopropyl trianthranil titanate, isoproopyl tri(N,N-dimethylethylamino)titanate, titanium-4-amino benzene sulfonat oxyacetate, titanium 4-aminobenzoate isostearate oxyacetate, $[H_2N(CH_2)_4]CH_3Si(OCH_3)_2$, (gamma-aminobutyl)methyl diethoxysilane, and $[H_2N(CH_2)_3]CH_3Si(OCH_3)_2$ (gamma-aminopropyl) methyl diethoxysilane, as disclosed in U.S. Pat. No. 4,291,110, 4,338,387, 4,286,033 and 4,291,110. The disclosures of U.S. Pat. No. 4,338,387, 4,286,033 and 4,291,110 are incorporated herein in their entirety. A preferred blocking layer comprises a reaction product between a hydrolyzed silane and the oxidized surface of a metal ground plane layer. The oxidized surface inherently forms on the outer surface of most metal ground plane layers when exposed to air after deposition. The blocking layer may be applied by any suitable conventional technique such as spraying, dip coating, draw bar coating, gravure coating, silk screening, air knife coating, reverse roll coating, vacuum deposition, chemical treatment and the like. For convenience in obtaining thin layers, the blocking layers are preferably applied in the form of a dilute solution, with the solvent being removed after deposition of the coating by conventional techniques such as by vacuum, heating and the like. The blocking layers should be continuous and have a thickness of less than about 0.2 micrometer because greater thicknesses may lead to undesirably high residual voltage.

An optional adhesive layer may applied to the hole blocking layer. Any suitable adhesive layer well known in the art may be utilized. Typical adhesive layer materials include, for example, polyesters, duPont 49,000 (available from E. I. duPont de Nemours and Company), Vitel PE100 (available from Goodyear Tire & Rubber), polyurethanes, and the like. Satisfactory results may be achieved with adhesive layer thickness between about 0.05 micrometer (500 angstrom) and about 0.3 micrometer (3,000 angstroms). Conventional techniques for applying an adhesive layer coating mixture to the charge blocking layer include spraying, dip coating, roll coating, wire wound rod coating, gravure coating, Bird applicator coating, and the like. Drying of the deposited coating may be effected by any suitable conventional technique such as oven drying, infra red radiation drying, air drying and the like.

Any suitable photogenerating layer may be applied to the adhesive blocking layer which can then be overcoated with a contiguous hole transport layer as described hereinafter. Examples of typical photogenerating layers include inorganic photoconductive particles such as amorphous selenium, trigonal selenium, and selenium alloys selected from the group consisting of selenium-tellurium, selenium-tellurium-arsenic, selenium arsenide and mixtures thereof, and organic photoconductive particles including various phthalocyanine pigment such as the X-form of metal free phthalocyanine described in U.S. Pat. No. 3,357,989, metal phthalocynines such as vanadyl phthalocyanine and copper phthalocyanine, dibromoanthanthrone, squarylium, quinacridones available from Dupont under the tradename Monastral Red, Monastral violet and Monastral Red Y, Vat orange 1 and Vat orange 3 trade names for dibromo anthanthrone pigments, benzimidazole perylene, substituted 2,4-diamino-triazines disclosed in U.S. Pat. No. 3,442,781, polynuclear aromatic quinones available from Allied Chemical Corporation under the tradename Indofast Double Scarlet, Indofast Violet Lake B, Indofast Brilliant Scarlet and Indofast Orange, and the like dispersed in a film forming polymeric binder. Multi-photogenerating layer compositions may be utilized where a photoconductive layer enhances or reduces the properties of the photogenerating layer. Examples of this type of configuration are described in U.S. Pat. No. 4,415,639, the entire disclosure of this patent being incorporated herein by reference. Other suitable photogenerating materials known in the art may also be utilized, if desired. Charge generating binder layers comprising particles or layers comprising a photoconductive material such as vanadyl phthalocyanine, metal free phthalocyanine, benzimidazole perylene, amorphous selenium, trigonal selenium, selenium alloys such as selenium-tellurium, selenium-tellurium-arsenic, selenium arsenide, and the like and mixtures thereof are especially preferred because of their sensitivity to white light. Vanadyl phthalocyanine, metal free phthalocyanine and selenium tellurium alloys are also preferred because these materials provide the additional benefit of being sensitive to infra-red light.

Any suitable polymeric film forming binder material may be employed as the matrix in the photogenerating binder layer. Typical polymeric film forming materials include those described, for example, in U.S. Pat. No. 3,121,006, the entire disclosure of which is incorporated herein by reference. Thus, typical organic polymeric film forming binders include thermoplastic and thermosetting resins such as polycarbonates, polyesters, polyamides, polyurethanes, polystyrenes, polyarylethers, polyarylsulfones, polybutadienes, polysulfones, polyethersulfones, polyethylenes, polypropylenes, polyimides, polymethylpentenes, polyphenylene sulfides, polyvinyl acetate, polysiloxanes, polyacrylates, polyvinyl acetals, polyamides, polyimides, amino resins, phenylene oxide resins, terephthalic acid resins, phenoxy resins, epoxy resins, phenolic resins, polystyrene and acrylonitrile copolymers, polyvinylchloride, vinylchloride and vinyl acetate copolymers, acrylate copolymers, alkyd resins, cellulosic film formers, poly(amideimide), styrene-butadiene copolymers, vinylidenechloride-vinylchloride copolymers, vinylacetate-vinylidenechloride copolymers, styrene-alkyd resins, polyvinylcarbazole, and the like. These polymers may be block, random or alternating copolymers.

The photogenerating composition or pigment is present in the resinous binder composition in various amounts, generally, however, from about 5 percent by volume to about 90 percent by volume of the photogenerating pigment is dispersed in about 10 percent by volume to about 95 percent by volume of the resinous binder, and preferably from about 20 percent by volume to about 30 percent by volume of the photogenerating pigment is dispersed in about 70 percent by volume to about 80 percent by volume of the resinous binder composition. In one embodiment about 8 percent by volume of the photogenerating pigment is dispersed in about 92 percent by volume of the resinous binder composition.

The photogenerating layer containing photoconductive compositions and/or pigments and the resinous binder material generally ranges in thickness of from about 0.1 micrometer to about 5.0 micrometers, and preferably has a thickness of from about 0.3 micrometer to about 3 micrometers. The photogenerating layer thickness is related to binder content. Higher binder content compositions generally require thicker layers for photogeneration. Thickness outside these ranges can be selected providing the objectives of the present invention are achieved.

Any suitable and conventional technique may be utilized to mix and thereafter apply the photogenerating layer coating mixture. Typical application techniques include spraying, dip coating, roll coating, wire wound rod coating, and the like. Drying of the deposited coating may be effected by any suitable conventional technique such as oven drying, infra red radiation drying, air drying and the like.

The active charge transport layer comprises an aromatic diamine or hydrazone charge transporting compound dissolved or molecularly dispersed in electrically inactive polystyrene film forming binder. The specific aromatic diamine or hydrazone charge transporting compound is added to polystyrene materials which are normally incapable of supporting the injection of photogenerated holes from the generation material and incapable of allowing the transport of these holes therethrough. This converts the electrically inactive polystyrene material to a material capable of supporting the injection of photogenerated holes from the generation material and capable of allowing the transport of these holes through the active layer in order to discharge the surface charge on the active layer. The expression "Electrically active" when used to define the charge transport layer means that the material is capable of supporting the injection of photogenerated holes from the generating material and capable of allowing the transport of these holes through the active layer in order to discharge a surface charge on the active layer. The expression "Electrically inactive" when used to describe the electrically inactive organic resinous binder material which does not contain any aromatic diamine or hydrazone compounds of the instant invention means that the binder material is not capable of supporting the injection of photogenerated holes from the generating material and is not capable of allowing the transport of these holes through the material. An especially preferred transport layer employed in one of the two electrically operative layers in the multilayered photoconductor of this invention comprises an aromatic diamine charge transporting compound and a polystyrene film forming resin in which the mixture aromatic amines is soluble. Without being limited by theory, it is believed that the interaction of the charge transporting donor molecules with polystyrene is different from that in polycarbonate due to the presence of polar groups in polycarbonate. It is possible that the strong dipole-dipole interaction between the polycarbonate polymer chains can hinder the proper alignment of the charge transporting donor molecules for easy charge exchange. Polystyrene like binders with no strong dipole groups are expected to yield the higher mobilities. The binder polymer compound may be represented by the general formula:

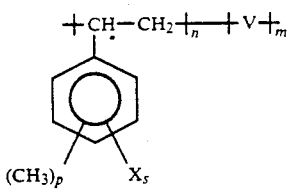

wherein:
n=0 to 1,
m=1 to 1,
m+n=1,
P=0, 1, 2 or 3,
X=—CN, Cl, Br, —CH$_2$CH$_3$, —CH(CH$_3$)$_2$, or —CH$_2$—CH$_2$—CH$_3$,
S=0, 1, 2 or 3,
P+S=0, 1, 2, 3 4 or 5,

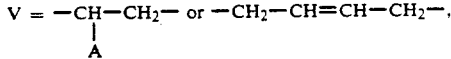

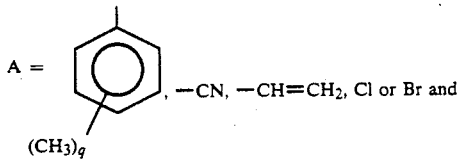

q=1, 2, or 3.

Typical polystyrene film forming binder materials represented by the above formula include, for example, poly(styrene), poly(p-methylstyrene), poly(2,4-methylstyrene),poly(p-chlorostyrene),poly(styrene-co-butadiene), poly(p-methylstyrene-co-butadiene), poly(styrene-co-isoprene), poly(styrene-co-vinylchloride), poly(styrene-co-acrylonitrile), poly(p-chlorostyrene-co-isoprene), poly(p-isopropylstyrene-co-styrene), poly(p-isopropylstyrene-co-acrylonitrile), poly(m-methylstyrene), poly(p-methoxystyrene), poly(p-methoxystyrene-co-vinylchloride) and the like.

The polystyrene film forming electrically inactive resin binder materials should have a weight average molecular weight between about 20,000 and about 5,000,000, more preferably between about 50,000 and about 300,000. When the weight average molecular weight is less than about 20000, the solution has poor viscosity resulting in difficult coating conditions. Also, the mechanical property of this coating is poor, resulting in cracks on the coating. Weight average molecular weights greater than about 5,000,000 can result in very high viscosities that render processing difficult.

The inactive polystyrene resin binder is soluble in methylene chloride, toluene, tetrahydrofuran, 1,1,2 dichloroethane, monochlorobenzene, mixtures thereof, and other suitable solvents.

The aromatic diamine charge transport layer compound may represented by the general formula:

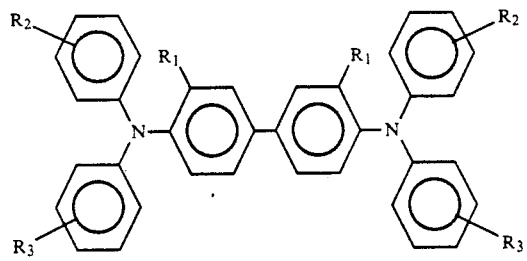

wherein R$_1$, R$_2$ and R$_3$ are independently selected from the group consisting of hydrogen, CH$_3$, C$_2$H$_5$, OCH$_3$, Cl and alkoxycarbonyl. Typical charge transporting aromatic amines represented by the structural formula above capable of supporting the injection of photogenerated holes and transporting the holes through the overcoating layer include N,N'-diphenyl-N,N'-bis(alkylphenyl)-(1,1'-biphenyl)-4,4'-diamine wherein the alkyl is, for example, methyl, ethyl, propyl, n-butyl, and the like, N,N'-diphenyl-N,N'-bis(chlorophenyl)-[1,1'-biphenyl-]-4,4'-diamine, N,N'-diphenyl-N,N'-bis(3-methylphenyl)-(1,1'-biphenyl)4,4'-diamine, N,N,N',N'-tetraphenyl-[3,3'-dimethyl-1,1'-biphenyl]-4,4'-diamine; N,N'-diphenyl-N,N'-bis(2-methylphenyl)-[3,3'-dimethyl-1,1'-biphenyl]-4,4'-diamine; N,N'-diphenyl-N,N'-bis(3-methylphenyl)-[3,3'-dimethyl-1,1'-biphenyl]-4,4'-diamine; N,N'-diphenyl-N,N'-bis(4-methylphenyl)-[3,3'-dimethyl-1,1'-biphenyl]-4,4'-diamine; N,N,N',N'-tetra(2-methylphenyl)-[3,3'-dimethyl-1,1'-biphenyl]-4,4'-diamine; N,N'-bis(2-methylphenyl)-N,N'-bis(4-methylphenyl)-[3,3'-dimethyl-1,1'-biphenyl]-4,4'-diamine; N,N'-bis(3-methylphenyl)-N,N'-bis(2-methylphenyl)-[3,3'-dimethyl-1,1'-biphenyl]-4,4'-diamine; N,N,N',N'-tetra(3-methylphenyl)-[3,3'-dimethyl-1,1'-biphenyl]-4,4'-diamine; N,N'-bis(3-methylphenyl)-N,N'-bis(4-methylphenyl)-[3,3'-dimethyl-1,1'-biphenyl]-4,4'-diamine; and N,N,N',N'-tetra(4-methylphenyl)-(3,3'-dimethyl-1,1'-biphenyl)-4,4'-diamine.

A preferred diamine is represented by the general formula:

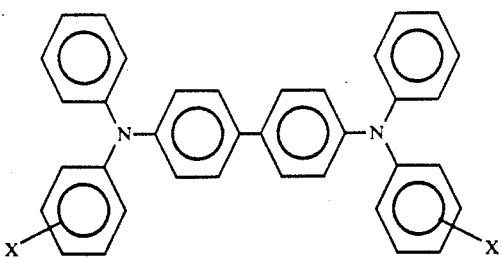

wherein X is selected from the group consisting of an alkyl group containing form 1 to 4 carbon atoms and chlorine. A specific preferred diamine is N,N,N',N'-Tetra-(4-methylphenyl)-[3,3'-dimethyl-1,1'-biphenyl]-4,4'-diamine which is represented by the formula:

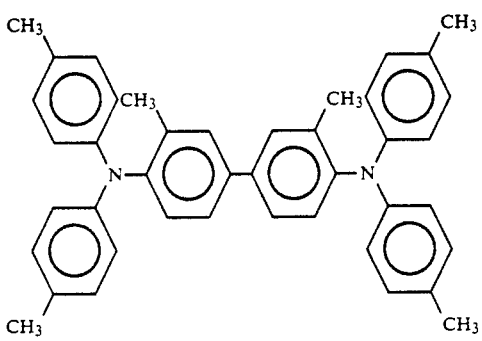

Another specific preferred diamine is N,N'-diphenyl-N,N'-bis(4-methylphenyl)-[3,3'-dimethyl-1,1'-biphenyl]-4,4'-diamine which is represented by the formula:

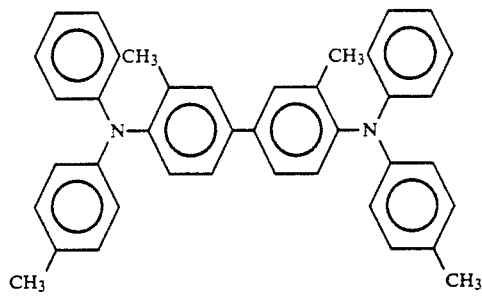

Still another specific preferred diamine is N,N'-bis(4-methylphenyl)-N,N'-bis(4-ethylene)-[3,3'-dimethyl-1,1'-biphenyl]-4,4'-diamine which is represented by the formula:

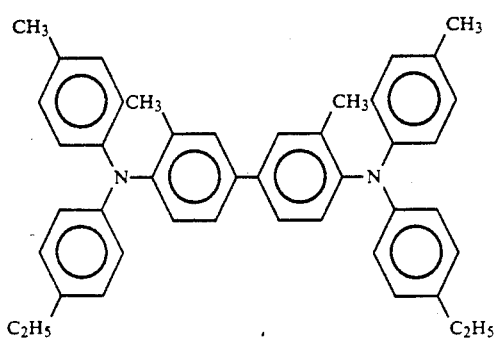

Satisfactory results may be achieved with between about 15 percent and about 75 percent by weight of the diamine based on the total weight of the diamines in the charge transport layer. Preferably, the charge transport layer of this invention contains between about 20 percent and about 60 percent by weight of the diamine based on the total weight of the diamines in the charge transport layer. When less about 20 percent by weight aromatic amine is employed, charge carrier mobilities are too low and therefore limit the speed of the xerographic process. Concentrations of this diamine greater than about 60 percent can result in crystallization of the transport layer. Specific aromatic diamine charge transport layer compounds encompassed by the formula above are described, for example, in U.S. Pat. Nos. 4,265,990, 4,299,897, and 4,833,054 the entire disclosures thereof being incorporated herein by reference. The substituents on aromatic diamine molecules should be free from electron withdrawing groups such as $NO_2$ groups, CN groups, and the like.

The hydrazone charge transport layer compound may represented by the general formula:

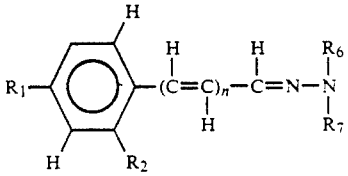

wherein
n = 1,

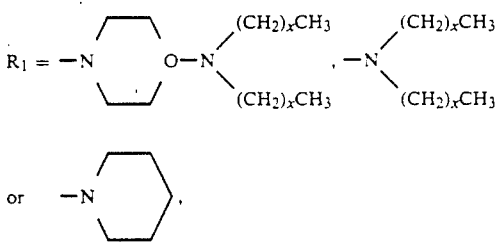

or

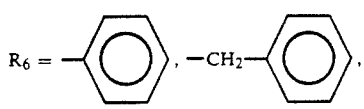

x = 0, 1, 2 or 3,
$R_2$ = —$OCH_2CH_3$, —$CH_3$ or —H,

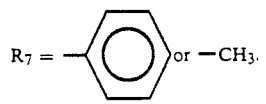

—$CH_3$ or
—$CH_2CH_2CH_2CH_3$, and $R_7$ = —⌬ or —$CH_3$.

Typical charge transporting hydrazones represented by the structural formula above capable of supporting the injection of photogenerated holes and transporting the holes through the overcoating layer include p-diethylaminobenzaldehyde-(diphenylhydrazone), o-ethoxy-p-diethylaminobenzaldehyde-(diphenylhydrazone), o-methyl-p-diethylaminobenzaldehyde-(diphenylhydrazone), o-methyl-p-dimethylaminobenzaldehyde-(diphenylhydrazone), p-dipropylaminobenzaldehyde-(diphenylhydrazone), ip-diethylaminobenzaldehyde-(benzylphenylhydrazone), p-dibutylaminobenzaldehyde-(diphenylhydrazone), p-dimethylaminobenzaldehyde-(diphenylhydrazone), 4,dimethylaminobenzaldehyde-1,2(diphenylhydrazone) and the like.

Satisfactory results may be achieved with between about 15 percent and about 75 percent by weight of the hydrazone based on the total weight of the hydrazone in the charge transport layer. Preferably, the charge transport layer of this invention contains between about 20 percent and about 60 percent by weight of the hydrazone based on the total weight of the diamines in the charge transport layer. When less about 20 percent by weight hydrazone is employed, charge carrier mobilities are too low and therefore limit the speed of the xerographic process. Concentrations of this hydrazone greater than about 60 percent can result in crystallization of the transport layer. Specific hydrazone charge transport layer compounds encompassed by the formula above are described, for example, in U.S. Pat. No. 4,150,987 the entire disclosure thereof being incorporated herein by reference. The substituents on hydrazone molecules should be free from electron withdrawing groups such as $NO_2$ groups, CN groups, and the like.

Any suitable and conventional technique may be utilized to mix and thereafter apply the charge transport layer coating mixture to the charge generating layer. Typical application techniques include spraying, dip coating, roll coating, wire wound rod coating, and the like. Drying of the deposited coating may be effected by any suitable conventional technique such as oven drying, infra radiation drying, air drying and the like. However, the charge transport coating mixture of this invention is particularly effective for dip or immersion coating techniques. This is because the maximum concentration of aromatic diamine that can be dispersed in a binder is limited in a dip coating process due to the long residence time of the solvent before the drying step occurs. Thus, phase separation of the diamine can occur during the solvent resident time. Phase separation is undesirable because phase separation results in poor charge transport including residual build which adversely affects print quality.

Surprisingly, the charge transport layers of this invention containing aromatic diamine and polystyrene can provide a charge carrier mobility value that can be considerably higher (thirtyfold) than the mobility values of conventional charge transport layers containing aromatic diamine and polycarbonate film forming binders such as those described, for example, in U.S. Pat. No. 4,265,990. This high mobility value renders operable small diameter cylindrical photoreceptors in high speed electrophotographic copier, duplicators and printers. More specifically, the time between exposure and development steps depends on the diameter of the rigid photoconductor substrate, the position of the development station with respect to the exposure subsystem and the surface velocity of the drum or the process speed. This time is equal to:

$$t_{ED} = \theta \times drum\ circumference/360 \times surface\ velocity$$

where $\theta$ is the angular position of the development station (measured from the physical center of the development zone) relative to the exposure station (measured from the physical center of the exposure zone). The physical center of the development zone is defined as the center of the zone adjacent the photoreceptor imaging surface between the point where development of a latent image begins and the point where development of a latent image terminates. Similarly, the physical center of the exposure zone is defined as the center of the zone adjacent the photoreceptor imaging surface between the point where exposure to form a latent image begins and the point where exposure to form a latent image terminates. Also, the erase station can be placed closer to the charging station as a result of the higher mobilities. This time ($t_{ED}$) decreases as the diameter of the drum decreases to decrease the size of the machine and the surface velocity increases to increase the number of copies per minute. The time ($t_{ED}$) elapsed between said exposing and the developing steps for the electrophotographic imaging processes of this invention can be as short between about 0.5 millisecond and about 500 milliseconds. Thus, for example, if the position of the development station relative to the exposure station is 20° with respect to the exposure station for an 84 mm diameter drum, the time between exposure station and the development station is 49 milliseconds for a 300 mm/sec process speed. These times become even smaller for a 40 mm diameter drum. Thus, an aromatic diamine, such as N,N'-diphenyl-N,N'-bis(3-methylphenyl)-(1,1'-biphenyl)-4,4'-diamine, at a 20 weight percent concentration in polycarbonates is not suitable for such applications, whereas the same concentration of the diamine in polystyrene is adequate for electrophotographic development to form toner images. Because of the high charge mobility capability of the photoreceptor of this invention, the time elapsed between the image exposure and image development steps can be as low as between about 0.5 millisecond and about 500 milliseconds. The high charge mobility capabilities of the photoreceptor of this invention also enable the use of rapidly rotating small diameter cylindrical photoreceptors having an outside diameter of between about 4.4 cm and about 8.4 cm. The outside diameter may be even smaller than 4.4 cm provided the other subsystems can be physically accommodated around the circumference. Thus, satisfactory results may be achieved at high speeds with cylindrical photoreceptors having an outside diameter between about 2.2 cm and about 12 cm. Preferably, the cylindrical photoreceptor has an outside diameter between about 4.4 cm and about 8.4 cm for high speed imaging.

Any suitable dip or immersion process may be employed for preparing the electrophotographic imaging member of this invention. The coating mixture is normally retained in a dip or immersion coating vessel and the cylindrical substrate to be coated and the vessel may be moved relative to the other. Thus, the substrate may be moved, the vessel may be moved or both may be moved. Generally, movement of the substrate and/or the vessel are effected in a vertical direction. Preferably, the coating mixture comprises between about 9 percent and about 12 percent by weight polystyrene film forming binder, between about 27 percent and about 3 percent by weight aromatic diamine or hydrazone, and between about 64 percent and about 85 percent by weight solvent for dip coating applications. Drying of the deposited coating may be accomplished by any suitable technique. Typical drying processes include, for example, oven drying, infrared radiation drying, forced air drying and the like.

Generally, the thickness of the hole transport layer is between about 10 about 50 micrometers, but thickness outside this range can also be used. The hole transport layer should be an insulator to the extent that the electrostatic charge placed on the hole transport layer is not conducted in the absence of illumination at a rate sufficient to prevent formation and retention of an electrostatic latent image thereon. In general, the ratio of thickness of the hole transport layer to the charge generator layer is preferably maintained from about 2:1 to 200:1 and in some instances as great as 400:1. In other words, the charge transport layer, is substantially non-absorbing to visible light or radiation in the region of intended use but is "active" in that it allows the injection of photogenerated holes from the photoconductive layer, i.e., charge generation layer, and allows these holes to be transported through the active charge transport layer to selectively discharge a surface charge on the surface of the active layer.

The photoreceptors of this invention may comprise, for example, a charge generator layer sandwiched between a conductive surface and a charge transport layer as described above or a charge transport layer sandwiched between a conductive surface and a charge generator layer. This structure may be imaged in the conventional xerographic manner which usually includes charging, optical exposure and development.

Other layers may also be used such as conventional electrically conductive ground strip along one edge of the belt or drum in contact with the conductive layer, blocking layer, adhesive layer or charge generating layer to facilitate connection of the electrically conductive layer of the photoreceptor to ground or to an electrical bias. Ground strips are well known and usually comprise conductive particles dispersed in a film forming binder.

Optionally, an overcoat layer may also be utilized to improve resistance to abrasion. In some cases an anti-curl back coating may be applied to the side opposite the photoreceptor to provide flatness and/or abrasion resistance. These overcoating and anti-curl back coating layers are well known in the art and may comprise thermoplastic organic polymers or inorganic polymers that are electrically insulating or slightly semiconductive. Overcoatings are continuous and generally have a thickness of less than about 10 micrometers.

Any suitable conventional electrophotographic charging, exposure, development, transfer, fixing and cleaning techniques may be utilize to form and develop electrostatic latent images on the imaging member of this invention. Thus, for example, conventional light lens or laser exposure systems may be used to form the electrostatic latent image. The resulting electrostatic latent image may be developed by suitable conventional development techniques such as magnetic brush, cascade, powder cloud, and the like. However, the rate at the photoreceptor surface is moved from an image exposure station and image development station is can be much higher than conventionally employed.

BRIEF DESCRIPTION OF THE DRAWINGS

Other objects and further features and advantages of this invention will be apparent from the following description considered with the accompanying drawing, wherein.

DETAILED DESCRIPTION OF THE DRAWING

Figure 1:
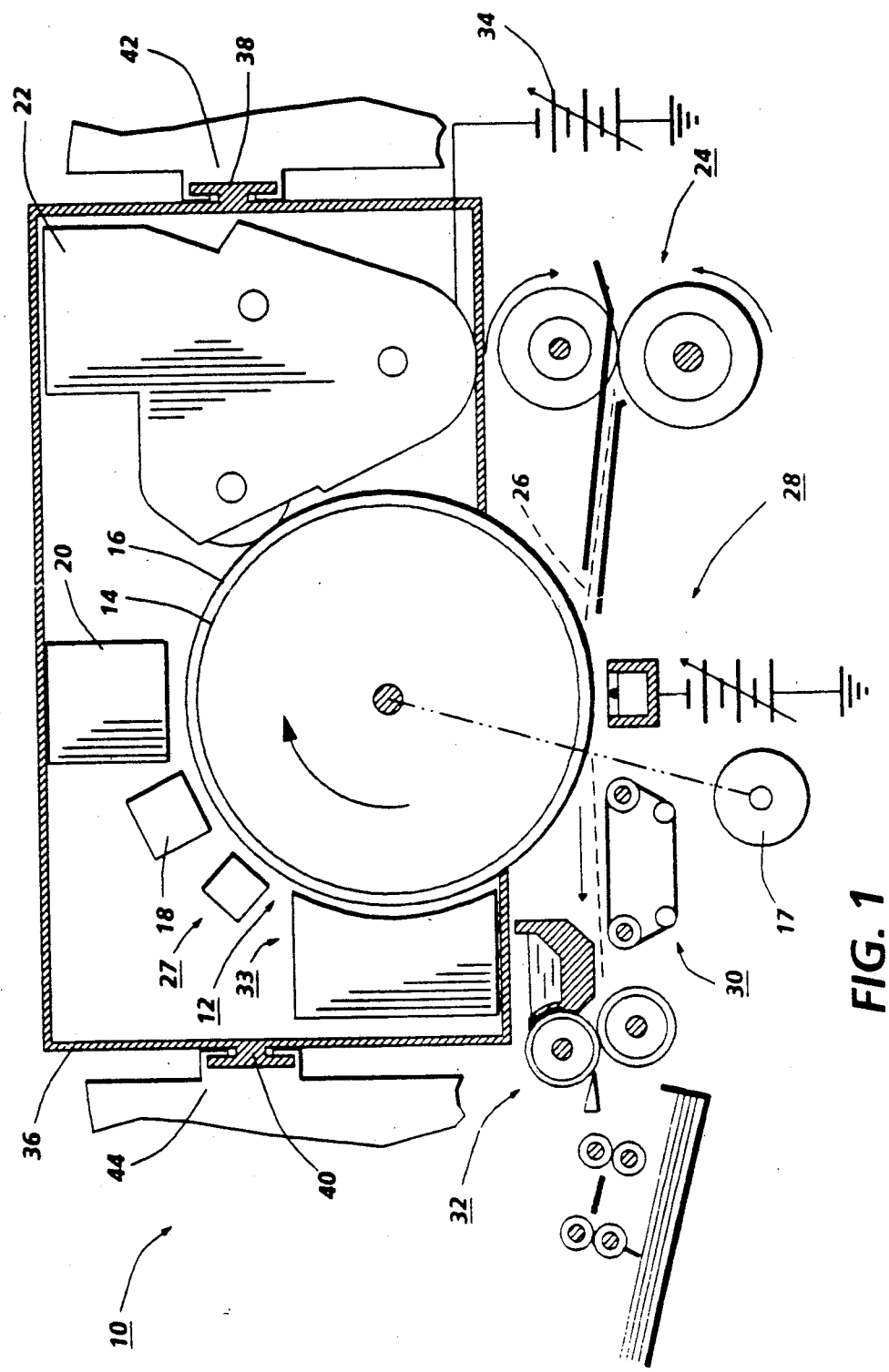
FIG. 1 is a partial sectional elevation view showing a simplified view of an electrophotographic imaging apparatus utilizing the photoreceptor of this invention.

Turing now to the drawing, there is illustrated in FIG. 1 an electrophotographic imaging system 10 comprising a cylindrical electrophotographic imaging member 12 comprising an electrically conductive drum 14 bearing a composite electrophotographic imaging layer 16 of this invention. Imaging member 12 is rotated by electric motor 17 through suitable linkages such as gears of belt and pulleys (represented by dashed line). Arranged around the outer periphery of electrophotographic imaging member 12 is a charging station 18 for applying a uniform electrostatic charge to the imaging layer 16; an exposure station 20 (e.g. laser or optical) for selectively discharging the uniformly charging imaging layer 16 to form an electrostatic latent image; a development station 22 (e.g. a magnetic brush applicator) for contacting the electrostatic latent image with two-component developer to a form a toner image in conformance with the electrostatic latent image; a sheet feeding station 24 to feed receiving sheets (shown as a dashed line 26) to imaging layer 16; an erase station 27 (e.g. flood exposure erase lamp); a transfer station 28 to transfer the toner image to receiving sheets 26; a sheet transport station 30 to transport receiving sheets 26 bearing the transferred toner imaging to a fusing station 32 for fixing the toner image to receiving sheets 26; and cleaning station 33 (e.g. blade, web or brush) for removing any residual toner remaining on imaging layer 16. An adjustable biasing power supply 34 connected to development station 22 permits changes to image development conditions relative to the latent image potential. By introducing a reverse bias, of the same polarity as the latent image, and applying the bias between the conductive drum 14 and the development station 22, non-uniformities in the non-image areas of the latent image can be kept more free of unwanted toner particles. Except for an opening at the bottom, cassette housing 36 surrounds and supports electrographic imaging member 12, charging station 18, exposure station 20, development station 22, and cleaning station 33. The bottom of cassette housing 36 is open to allow imaging layer 16 to contact receiving sheets. Rails 38 and 40 are secured to the sides of and support cassette housing 36 and are adapted to be slideably mounted in horizontal tracks 42 and 44, respectively, which are, in turn, secured to frame members of the printing device. A suitable latching means (not shown) temporarily retains the cassette in place relative to the path of the receiving sheets. This arrangement facilitates rapid replacement of the major components of the electrographic printing engine. If desired, one or more of the processing stations may be positioned outside of cassette housing 36 and mounted to the frame members of the printing device because replacement is unnecessary at the time the electrographic imaging member 12 is replaced. All of the stations positioned around the periphery of electrophotographic imaging member 12 are conventional and well known in the art. However, in order, to fit around very small diameter drums, the size of the stations may necessarily be smaller than normal, particularly drums having a diameter between about 4.4 cm and about 8.4 cm.

The mixture of active aromatic amino charge transport compounds or hydrazone charge transport compounds and polystyrene in the charge transport layer of the photoreceptor of this invention exhibits surprisingly high charge carrier mobility. Greater charge carrier mobility capacities are exhibited at lower concentrations of the active small molecule transport compound dissolved or molecularly dispersed in the polystryene binder. Also, higher concentrations of active aromatic diamine small molecular charge transport compounds or hydrazone charge transport compounds may be achieved with less tendency to crystallize as the concentration of the active diamine transport compound is increased in polystyrene binder, particularly when applied as a solution by dip coating techniques. Thus, the charge transport layers of this invention may be applied to photoreceptors by dip coating without exceeding the maximum concentration limit set by the onset of crystallization in the transport layer. Therefore, the high charge carrier mobility of the photoreceptors of this invention greatly chances the processing speed of electrophotographic copier, duplicators and printers.

A number of examples are set forth hereinbelow and are illustrative of different compositions and conditions that can be utilized in practicing the invention. All proportions are by weight unless otherwise indicated. It will be apparent, however, that the invention can be practiced with many types of compositions and can have many different uses in accordance with the disclosure above and as pointed out hereinafter.

EXAMPLE I

An electrophotographic imaging member was prepared by forming coatings using conventional coating techniques on a suitable comprising vacuum deposited titanium layer on a polyethylene terephthalate film (Mylar, available from E. I. duPont de Nemours & Co.). The first coating was a siloxane barrier layer formed from hydrolyzed gamma aminopropyltriethoxysilane having a thickness of 50 angstroms. This film was coated as follows: 3-aminopropyltriethoxysilane (available for PCR Research Chemicals of Florida) was mixed in ethanol in a 1:50 volume ratio. The film was applied to a wet thickness of 0.5 mil of a multiple clearance film applicator. The layer was then allowed to dry for 5 minutes at room temperature, followed by curing for 10 minutes at 110 degree centigrade in a force air oven. The second coating was an adhesive layer of polyester resin (49,000, available from E. I. duPont de Nemours & Co.) having a thickness of 50 angstroms and was coated as follows: 0.5 grams of 49,000 resin was dissolved in 70 grams of tetrahydrofuran and 29.5 grams of cyclohexanone. The film was coated by a 0.5 mil bar and cured in a forced air oven for 10 minutes. The next coating was a charge generator layer containing 35 percent by weight vanadyl phthalocyanine particles dispersed in a polyester resin (Vitel PE100, available from Goodyear Tire and Rubber Co.) having a thickness of 1 micrometer and was coated as follows: 0.35 gram of vanadyl phthalocyanine pigment and 0.65 gram of polyester (Vitel PE100, available from Goodyear Tire & Rubber Co.) were roll milled for 24 hours employing stainless steel shot in a mixture of solvents containing 12.4 grams of methylene chloride and 5.8 grams of dichloroethane. The film was coated utilizing a 0.5 mil bar and cured at 100 degree centigrade for 10 minutes. The top coating was a charge transport layer of a dispersion of aromatic diamine donor molecules in polycarbonate resin (Makrolon, available from Farbenfabricken Bayer A.G.) having a thickness of 20 micrometers. The transport layer was fabricated by first dissolving two grams of Makrolon ® polycarbonate and 0.5 gram of the aromatic diamine, N,N'-diphenyl-N,N'-bis(3-methylphenyl)-(1,1'-biphenyl)-4,4'-diamine (Diamine, 1), in 22.8 grams of methylene chloride. After dissolution, the mixture was coated on the substrate containing the charge generator layer using a 3 mil Bird film applicator. The film was dried in a forced air oven at 100° C. for 20 minutes. The device was tested for charge carrier mobility by employing the time of flight technique. The time of flight experiments were carried out on a sandwich structure consisting of the electrically conductive titanium coated substrate, the barrier layer, the adhesive layer, the charge generator layer and the charge transport layer (the devices under study) and a vacuum deposited semi-transparent gold electrode. This sandwich was connected in a circuit containing a voltage power supply and a current measuring series resistance. The principal underlying this time of flight test is that when the gold electrode is biased negatively and the device exposed to a flash of light, holes photogenerated in the generator layer are injected into and drift through the transport layer. The electric current due to the carrier transit is time resolved and displayed on an oscilloscope. A constant current followed by a sharp drop-off was observed. The point at which the sharp drop occurs is the transit time. The transit time $t_{tr}$ is equal to the thickness of the transport layer divided by velocity, i.e. $t_{tr}=$(TL thickness)/velocity. The relationship between the velocity and charge carrier mobility is velocity=(mobility)·(electric field). The formulations of the transport layers of the device and the results of the time of flight experiments carried out on the device is tabulated in the Table 1 below in Example II.

EXAMPLE II

A device was fabricated similar to that in Example I, except for the transport layer. The transport layer of this device consisted of the same aromatic diamine of Example I dispersed in polystyrene having a molecular weight of 80,000. The transport layer was fabricated by dissolving 1.73 grams of polystyrene and 0.5 gram of the aromatic diamine N,N'-diphenyl-N,N'-bis(3-methylphenyl)-(1,1'-biphenyl)-4,4'-diamine in 22.8 grams of methylene chloride. At the weight concentrations of this system, the molecular concentration (the number of diamine molecules per $cm^3$) is the same as that in Example I. After dissolution, the mixture was coated on the substrate containing the charge generator layer using a 3 mil Bird film applicator. The film was dried in a forced air oven at 100° C. for 20 minutes. The device was tested for charge carrier mobility by employing the time of flight technique described in Example I. The formulations of the transport layers of this device and the device of Example I along with the results of the time of flight experiments carried out on the device are tabulated in Table 1 below.

TABLE 1

| Device | Transport Layer Composition (wt. of Diamine 1 in one cubic cm of resin) | RESIN | Hole Mobility in $Cm^2$/Volt Second At $10^5$ Volts/cm |
| --- | --- | --- | --- |
| Example I | 0.3 gm | Polycarbonate | $3.2 \times 10^{-8}$ |
| Example II | 0.3 gm | Polystyrene | $6.7 \times 10^{-7}$ |

The results show a totally unexpected, more than twentyfold increase in charge carrier velocities by replacing polycarbonate with polystyrene. The use of polystyrene, therefore, allows a dramatic increase in the process speed of the xerographic process as demonstrated in the next example, Example III.

EXAMPLE III

Devices identical to those described in Examples I and II, but without the gold electrode, were mounted in a scanner and tested to determine the relative process speeds to develop contrast potentials. The device was mounted on a cylindrical aluminum drum which was rotated on a shaft. The film was charged by a corotron mounted along the circumference of the drum. The surface potential was measured as a function of time by several capacitively coupled probes placed at different locations around the shaft. The probes were calibrated by applying known potentials to the drum substrate. The film on the drum was exposed and erased by light sources located at appropriate positions around the drum. The measurement consisted of charging the photoconductor device in a constant current or voltage mode. As the drum rotated, the initial charging potential was measured by probe 1. Further rotation led to the exposure station, where the photoconductor device was exposed to monochromatic radiation of known intensity. The surface potential after exposure was measured by probes 2 and 3. The device was finally exposed to an erase lamp of appropriate intensity and any residual potential was measured by probe 4. The process was repeated with the magnitude of the exposure automatically changed during the next cycle. A photo induced discharge characteristics (PIDC) was obtained by plotting the potentials at probes 2 and 3 as a function of exposure. The two devices were charged to a negative polarity by corotron charging and discharged by monochromatic light in the visible and in the IR portion of the light spectrum. The initial potential and the potential at 50 milliseconds after exposure to a flash of light were measured and tabulated in Table 2.

TABLE 2

| Device | Transport Layer Composition (wt. of Diamine 1 in one cubic cm of resin) | RESIN | Initial Potential | Potential 50 milli sec. after exposure |
|---|---|---|---|---|
| Example I | 0.3 gm | Polycarbonate | 1000 V | 950 V |
| Example II | 0.3 gm | Polystyrene | 1000 V | 220 V |

The results show that devices with transport layers containing molecular dispersions of charge transporting aromatic diamine in polystyrene can be employed in machines operating at significantly higher speeds. This result is totally unexpected.

EXAMPLE IV

A device was fabricated similar to the device in Example I, except for the transport layer. The transport layer of this device consisted of the same aromatic diamine of Example 1 dispersed in Makrolon ® at a higher molecular concentration than in Example I. The transport layer was fabricated by dissolving 1.25 grams of Makrolon ® and 1.25 grams of the aromatic diamine N,N'-diphenyl-N,N'-bis(3-methylphenyl)-(1,1'-biphenyl)-4,4'-diamine in 22.8 grams of methylene chloride. After dissolution, the mixture was coated on the substrate containing the charge generator layer using a 3 mil Bird film applicator. The film was dried in a forced air oven at 100° C. for 20 minutes. The device was tested for charge carrier mobility by employing the time of flight technique described in Example I. The formulations of the transport layers of the device and the results of the time of flight experiments carried out on the device are tabulated in the Table 3 below in Example V.

EXAMPLE V

A device was fabricated similar to the device in Example I, except for the transport layer. The transport layer of this device consisted of the same aromatic diamine of Example IV dispersed in polystyrene. The transport layer was fabricated by dissolving 1.08 grams of polystyrene and 1.25 grams of the aromatic diamine N,N'-diphenyl-N,N'-bis(3-methylphenyl)-(1,1'-biphenyl)-4,4'-diamine in 22.8 grams of methylene chloride. At the weight concentrations of this system, the molecular concentration (the number of diamine molecules per $cm^3$) is the same as that in Example IV. After dissolution, the mixture was coated on the substrate containing the charge generator layer using a 3 mil Bird film applicator. The film was dried in a forced air oven at 100° C. for 20 minutes. The device was tested for charge carrier mobility by employing the time of flight technique described in Example I. The formulations of the transport layers of the device and the results of the time of flight experiments carried out on the device is tabulated in the Table 3 below.

TABLE 3

| Device | Transport Layer Composition (wt. of Diamine 1 in one cubic cm of resin) | RESIN | Hole Mobility in $Cm^2$/Volt Second At $10^5$ Volts/cm |
|---|---|---|---|
| Example IV | 1.2 gm | Polycarbonate | $1.8 \times 10^{-5}$ |
| Example V | 1.2 gm | Polystyrene | $5.4 \times 10^{-5}$ |

The mobility value was considerably higher when polystyrene was substituted for Makrolon ®. The results show that devices with transport layers containing molecular dispersions of charge transporting aromatic diamine in polystyrene can be employed in machines operating at significantly higher speeds. This result is totally unexpected.

EXAMPLE VI

Devices identical to those described in Examples IV and V, but without the gold electrode, were mounted in a scanner and tested to determine the relative process speeds to develop contrast potentials. The device was mounted on a cylindrical aluminum drum which was rotated on a shaft. The test carried out as described in Example III. The two devices were charged to a negative polarity by corotron charging and discharged by monochromatic light in the visible and in the IR portion of the light spectrum. The initial potential and the potential at 5 milliseconds after exposure to a flash of light were measured and tabulated in Table 4 below.

TABLE 4

| Device | Transport Layer Composition (wt. of Diamine 1 in one cubic cm of resin) | RESIN | Initial Potential | Potential 5 milli sec. after exposure |
|---|---|---|---|---|
| Example IV | 1.2 gm | Polycarbonate | 1000 V | 100 V |
| Example V | 1.2 gm | Polystyrene | 1000 V | 30 V |

The results show that devices with transport layers containing molecular dispersions of charge transporting aromatic diamine in polystyrene can be employed in machines operating at significantly higher speeds. This result is totally unexpected.

EXAMPLE VII

A device was fabricated similar to that in Example I, except for the transport layer. The transport layer of this device consisted of an aromatic diamine that was different from that employed in Examples I through VI, dispersed in Makrolon ®. The transport layer was fabricated by dissolving 1.916 grams of Makrolon ® and 0.583 gram of the aromatic diamine N,N'-bis(4-methylphenyl)-N,N'-bis(4-ethylphenyl)-[3,3'-dimethyl-1,1'-biphenyl]-4,4'-diamine (diamine 2) in 22.8 grams of methylene chloride. After dissolution, the mixture was coated on the substrate containing the charge generator layer using a 3 mil Bird film applicator. The film was dried in a forced air oven at 100° C. for 20 minutes. The device was tested for charge carrier mobility by employing the time of flight technique described in Example I. The formulations of the transport layers of the device and the results of the time of flight experiments carried out on the device is tabulated in the Table 5 below in Example VIII.

EXAMPLE VIII

A device was fabricated similar to that in Example VII, except for the transport layer. The transport layer of this device consisted of the same aromatic diamine of Example VII dispersed in polystyrene. The transport layer was fabricated by dissolving 1.66 grams of polystyrene and 0.583 grams of the aromatic diamine N,N'-bis(4-methylphenyl)-N,N'-bis (4-ethylphenyl)-[3,3'-dimethyl-1,1'-biphenyl]-4,4'-diamine (diamine 2) in 22.8 grams of methylene chloride. At the weight concentrations of this system, the molecular concentration (the number of diamine molecules per cm$^3$) was the same as that in Example VII. After dissolution, the mixture was coated on the substrate containing the charge generator layer using a 3 mil Bird film applicator. The film was dried in a forced air oven at 100° C. for 20 minutes. The device was tested for charge carrier mobility by employing the time of flight technique described in Example I. The formulations of the transport layers of the device and the results of the time of flight experiments carried out on the device is tabulated in the Table 5 below.

TABLE 5

| Device | Transport Layer Composition (wt. of Diamine 2 in one cubic cm of resin) | RESIN | Hole Mobility in Cm$^2$/Volt Second At 10$^5$ Volts/cm |
|---|---|---|---|
| EXAMPLE VII | 0.36 gm | Polycarbonate | $4.4 \times 10^{-7}$ |
| EXAMPLE VIII | 0.36 gm | Polystyrene | $1.5 \times 10^{-5}$ |

The mobility value is considerably higher (more than thirtyfold) when polystyrene is substituted for Makrolon ®. The results show that devices with transport layers containing molecular dispersions of charge transporting aromatic diamine in polystyrene can be employed in machines operating at significantly higher speeds. This result is totally surprising and unexpected.

EXAMPLE IX

Devices identical to those described in Examples VII and VIII, but without the gold electrode, were mounted in a scanner and tested to determine the relative process speeds to develop contrast potentials. The device was mounted on a cylindrical aluminum drum which was rotated on a shaft. The procedure for measuring the sensitivity and speed are described in Example III. The two devices were charged to a negative polarity by corotron charging and discharged by monochromatic light in the visible and in the IR portion of the light spectrum. The initial potential and the potential at 50 milliseconds after exposure to a flash of light were measured and tabulated in Table 6 below.

TABLE 6

| Device | Transport Layer Composition (wt. of Diamine 2 in one cubic cm of resin) | RESIN | Initial Potential | Potential 50 milli sec. after exposure |
|---|---|---|---|---|
| Example VII | 0.36 gm | Polycarbonate | 1000 V | 950 V |
| Example VIII | 0.36 gm | Polystyrene | 1000 V | 30 V |

The results show that devices with transport layers containing molecular dispersions of charge transporting aromatic diamine in polystyrene can be employed in machines operating at significantly higher speeds. This result is totally unexpected.

EXAMPLE X

A device was fabricated similar to that in Example I, except for the transport layer. The transport layer of this device consisted of the same aromatic diamine of Examples VII through IX dispersed in Makrolon ® at a higher molecular concentration than in Examples VII through IX. The transport layer was fabricated by dissolving 1.038 grams of Makrolon ® and 1.458 grams of the aromatic diamine N,N'-bis(4-methylphenyl)-N,N'-bis(4-ethylphenyl)-[3,3'-dimethyl-1,1'-biphenyl]-4,4'-diamine (Diamine 2) in 22.8 grams of methylene chloride. After dissolution, the mixture was coated on the substrate containing the charge generator layer using a 3 mil Bird film applicator. The film was dries in a forced air oven at 100° C. for 20 minutes. The device was tested for charge carried mobility by employing the time of flight technique described in Example I. The formulations of the transport layers of the device and the results of the time of flight experiments carried out on the device are tabulated in Table 7 below in Example XI.

EXAMPLE XI

A device was fabricated similar to that in Example X, except for the transport layer. The transport layer of this device consisted of the same aromatic diamine of Example X dispersed in polystyrene. The transport layer was fabricated by dissolving 0.9 gram of polystyrene and 1,458 grams of the aromatic diamine N,N'-bis(4-methylphenyl)-N,N'-bis (4-ethylphenyl)-[3,3'-dimethyl-1,1'-biphenyl]-4,4'-diamine (Diamine 2) in 22.8 grams of methylene chloride. At the weight concentrations of this system the molecular concentration (the number of diamine molecules per $cm^3$) is the same as that in Example X. After dissolution, the mixture was coated on the substrate containing the charge generator layer using a 3 mil Bird film applicator. The film was dried in a forced air oven at 100° C. for 20 minutes. The device was tested for charge carrier mobility by employing the time of flight technique described in Example I. The formulations of the transport layers of the device and the results of the time of flight experiments carried out on the device are tabulated in the Table 7 below.

TABLE 7

| Device | Transport Layer Composition (wt. of Diamine 2 in one cubic cm of resin) | RESIN | Hole Mobility in $Cm^2$/Volt Second At $10^5$ Volts/cm |
| --- | --- | --- | --- |
| Example X | 1.69 gm | Polycarbonate | $1.66 \times 10^{-5}$ |
| Example XI | 1.69 gm | Polystyrene | $4.7 \times 10^{-4}$ |

The mobility value is considerably higher (thirtyfold) when polystyrene is substituted for Makrolon ®. The results show that devices with transport layers containing molecular dispersions of charge transporting aromatic diamine in polystyrene can be employed in machines operating at significantly higher speeds. This result is totally unexpected and surprising.

EXAMPLE XII

The mobility value of devices in Examples X and XI (Table 7) indicate that the transport layer of diamine 2 in polystyrene can be employed in machines with process speeds over 30 times faster than when the diamine 2 is dispersed in polycarbonate. This result is totally surprising and unexpected.

EXAMPLE XIII

The time between exposure and development steps depends on the diameter of the rigid photoconductor substrate, the position of the development station with respects to the exposure subsystem and the surface velocity of the drum or the process speed. This time is equal to:

$$t_{ED} = \theta \times \text{drum circumference}/360 \times \text{surface velocity}$$

where $\theta$ is the angular position of the development station relative to the exposure station. This time decreases as the diameter of the drum decreases to decrease the size of the machine end the surface velocity increases to increase the number of copies per minute. For an 84 mm diameter drum if the position of the development station relative to the exposure station is 20° with respect to the exposure station, the time between exposure station and the development station is 49 milliseconds for a 300 mm/sec process speed. These times become even smaller for a 40 mm diameter drum. The results in Table 2 indicate that Diamine 1 at a 20 weight percent concentration in polycarbonate is not suitable for such applications, whereas the same concentration of diamine in polystyrene is adequate for electrophotographic development to form toner images. The maximum concentration of diamine that can be dispersed in a binder is limited in a dip coating process due to the long residence time of the solvent before the drying step and the phase separation that occurs during the solvent resident time.

EXAMPLE XIV

This example illustrates the stability of the transport layers of this invention when exposed to ultraviolet radiation. A transport layer was prepared by forming coatings using conventional coating techniques on a substrate comprising a vacuum deposited titanium layer on a polyethylene terephthalate film (Mylar, available from E. I. duPont de Nemours & Co.). The first coating applied to the titanium layer was a siloxane barrier layer formed from hydrolyzed gamma aminopropyltriethoxysilane having a dried thickness of 50 angstroms. This film was coated as follows: 3-aminopropyltriethoxysilane (available from PCR Research Chemicals of Florida) was mixed in ethanol in a 1:50 volume ratio. The film was applied to a wet thickness of 0.5 mil by a multiple clearance film applicator. The layer was then allowed to dry for 5 minutes at room temperature, followed by curing for 10 minutes at 110 degree centigrade in a forced air oven. The second coating was an adhesive layer of polyester resin (49,000, available from E. I. duPont de Nemours & Co.) having a thickness of 50 angstroms and was applied as follows: 0.5 gram of 49,000 resin was dissolved in 70 grams of tetrahydrofuran and 29.5 grams of cyclohexanone. The film was coated using a 0.5 mil bar and cured in a forced air oven for 10 minutes. The next coating was a charge transport layer of a dispersion of aromatic diamine donor molecules in polycarbonate resin (Makrolon, available from Farbenfabricken Bayer A.G.) having a thickness of 20 micrometers. The transport layer was fabricated by first dissolving 1.25 grams of Makrolon ® polycarbonate and 1.25 grams of the aromatic diamine, N,N'-diphenyl-N,N'-bis(3-methylphenyl)-(1,1'-biphenyl)-4,4'-diamine (Diamine 1), in 22.8 grams of methylene chloride. After dissolution, the mixture was coated on the substrate containing the first two coatings using a 3 mil Bird film applicator. The film was dried in a forced air oven at 100° C. for 20 minutes. The transport layer was tested for it's conductivity by negatively charging the device to 1000 volts and monitoring the drop in potential in the dark for 2 minutes. The drop in potential was 30 volts. The layer was subsequently exposed to a long wavelength UV radiation ($3000A^0$–$4000A^0$) source for 1 hour. The total UV photon flux was approximately $10^{18}$ photons/$cm^2$. The transport layer was negatively charged to 1000 volts and the dark decay in 2 minutes was 500 volts. The transport layer had become significantly more conductive as a result of UV exposure.

EXAMPLE XV

A transport layer similar to that in Example XIV was fabricated except for the transport layer binder. The transport layer of the instant device consisted of the same aromatic diamine of Example XIV dispersed in polystyrene having a molecular weight of 80,000. The transport layer was fabricated by dissolving 1.08 grams of polystyrene and 1.25 grams of the aromatic diamine, N,N'-diphenyl-N,N'-bis(3-methylphenyl)-(1,1'-biphenyl)-4,4'-diamine, in 22.8 grams of methylene chloride. At the weight concentrations of this system, the molecular concentration (the number of diamine molecules per cm$^3$) is the same as that in Example XIV. After dissolution, the mixture was coated on the substrate containing the first two coatings using a 3 mil Bird film applicator. The film was dried in a forced air oven at 100° C. for 20 minutes. The transport layer was tested for it's conductivity by negatively charging the device to 1000 volts and monitoring the drop in potential in the dark for 2 minutes. The drop in potential was 30 volts. The layer was subsequently exposed to a long wavelength UV radiation (3000A$^0$–4000A$^0$) source for 1 hour. The total UV photon flux was approximately 10$^{18}$ photons/cm$^2$. The transport layer was negatively charged to 1000 volts and the dark decay in 2 minutes was unchanged and remained at 30 volts. This demonstrated that the transport layer of this invention is stable after exposure to UV radiation.

EXAMPLE XVI

A device was fabricated similar to the device in Example I, except for the transport layer. The transport layer of this device consisted of 4,diethylaminobenzaldlhyde-1,2 diphenylhydrazone dispersed in Makrolon$^R$. The transport layer was fabricated by dissolving 1.68 grams of Makrolon® and 0.83 grams of 4,diethylaminobenzaldehyde-1,2diphenylhydrazone in 22.8 grams of methylene chloride. After dissolution, the mixture was coated on the substrate containing the charge generator layer using a 3 mil Bird film applicator. The film was dried in a forced air oven at 20° C. for 240 minutes. The device was tested for charge carrier mobility by employing the time of flight technique described in Example I. The formulations of the transport layers of the device and the results of the time of flight experiments carried out on the device are tabulated in the Table 8 below in Example XVII.

EXAMPLE XVII

A device was fabricated similar to the device in Example XVI except for the transport layer. The transport layer of the device consisted of the same hydrazone of Example XVI dispersed in polystyrene. The transport layer was fabricated by dissolving 1.45 grams of polystyrene and 0.83 grams of the hydrazone, 4,diethylaminobenzaldehyde-1,2 diphenylhydrazone in 22.8 grams of methylene chloride. At the weight concentrations of this system, the molecular concentration (the number of hydrazone molecules per cm$^3$) is the same as that in Example XVI. After dissolution, the mixture was coated on the substrate containing the charge generator layer using a 3 mil Bird film applicator. The film was dried in a forced air oven at 20° C. for 240 minutes. The device was tested for charge carrier mobility by employing the time of flight technique described in Example I. The formulations of the transport layers of the device and the results of the time of flight experiments carried out on the device is tabulated in the Table 8 below.

TABLE 8

| Device | Transport Layer Composition (wt. of hydrazone in one cubic cm of resin) | RESIN | Hole Mobility in Cm$^2$/Volt Second At 10$^5$ Volts/cm |
|---|---|---|---|
| Example XVI | 0.59 gm | Polycarbonate | $1.5 \times 10^{-7}$ |
| Example XVII | 0.59 gm | Polystyrene | $5 \times 10^{-7}$ |

The charge carrier mobility of hydrazone in polystyrene is significantly higher than that in polycarbonate.

Although the invention has been described with reference to specific preferred embodiments it is not intended to be limited thereto, rather those skilled in the art will recognize that variations and modifications may be made therein which are within the spirit of the invention and within the scope of the claims.

What is claimed is:

1. An electrophotographic imaging process comprising providing an electrophotographic imaging member comprising a charge generating layer and a charge transport layer, said charge transport layer comprising polystyrene film forming binder and a charge transport molecule selected from the group consisting of an aromatic diamine represented by the general formula:

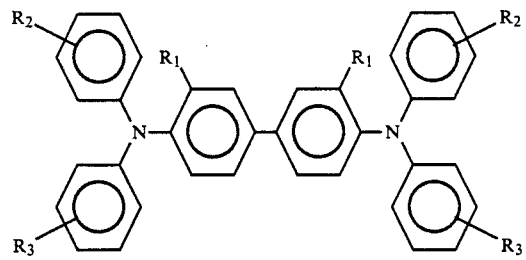

wherein R$_1$ represents hydrogen, an alkyl group or an alkoxy group, R$_2$ represents a hydrogen atom, an alkyl group, an alkoxy group, a halogen atom, an alkoxycarbonyl group or a substituted amino group and R$_3$ represents an alkyl group, an alkoxy group, an alkoxy group, a halogen atom, an alkoxycarbonyl group or a substituted amino group, and a hydrazone represented by the general formula:

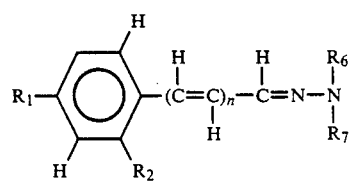

wherein
n=1,

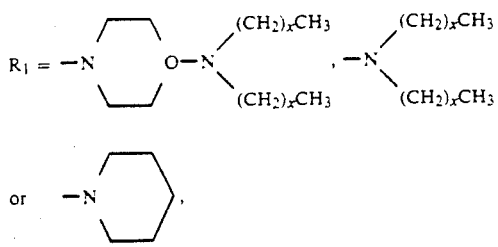

x=0,1,2, or 3,
$R_2 =$ —OCH$_2$CH$_3$, —CH$_3$ or —H,

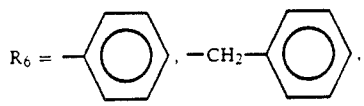

—CH$_3$ or —CH$_2$CH$_2$CH$_2$CH$_3$, and

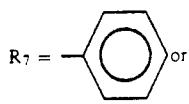

—CH$_3$, depositing a uniform electrostatic charge on said imaging member with a corona charging device, exposing said imaging member to activating radiation in image configuration to form an electrostatic latent image on said imaging member, developing said electrostatic latent image with electrostatically attractable marking particles to form a toner image, transferring said toner image to a receiving member and repeating said depositing, exposing, developing and transfering steps, the time elapsed between said exposing and the developing steps is between about 0.5 millisecond and about 500 milliseconds.

2. An electrophotographic imaging process according to claim 1 wherein said charge transport layer comprises between about 15 percent and about 75 percent by weight of said aromatic diamine based on the total weight of said charge transport layer.

3. An electrophotographic imaging process according to claim 2 wherein said charge transport layer comprises between about 20 percent and about 60 percent by weight of said aromatic diamine based on the total weight of said charge transport layer.

4. An electrophotographic imaging process according to claim 1 wherein said polystyrene has a weight average molecular weight between about 20,000 and about 5,000,000.

5. An electrophotographic imaging process according to claim 1 wherein the time elapsed between said exposing and the developing steps is between about 1 millisecond and about 200 milliseconds.

6. An electrophotographic imaging process according to claim 1 wherein said charge transport layer is between a conductive surface and said charge generating layer.

7. An electrophotographic imaging process according to claim 1 wherein said charge generating layer is between a conductive surface and said charge transport layer.

8. An electrophotographic imaging process according to claim 1 wherein said aromatic diamine is represented by the general formula:

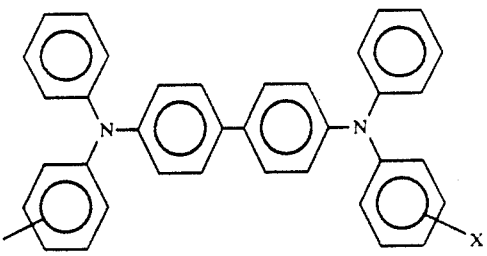

wherein X is selected from the group consisting of an alkyl group containing from 1 to 4 carbon atoms and chlorine.

9. An electrophotographic imaging process according to claim 1 wherein said electrophotographic imaging member comprises a rigid cylindrical substrate coated with said charge generating layer and said charge transport layer.

10. An electrophotographic imaging process according to claim 9 wherein said electrophotographic member has an outside diameter of between about 2.2 cm and about 12 cm.

11. An electrophotographic imaging process according to claim 10 wherein said electrophotographic imaging member has an outside diameter of between about 4.4 cm and about 8.4 cm.

12. An electrophotographic imaging process according to claim 1 wherein said polystyrene is represented by the general formula:

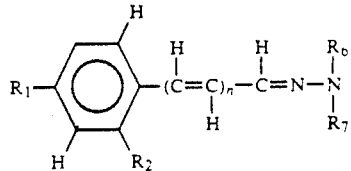

wherein:
n=0 to 1,
m=0 to 1
m+n=1,
P=0,1,2 or 3,
X= —CN,Cl,Br,—CH$_2$CH$_3$, —CH(CH$_3$)$_2$, or —CH$_2$—CH$_2$—CH$_3$;
S=0,1,2 or 3,
p+S=0,1,2,3,4 or 5

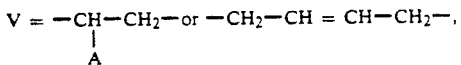

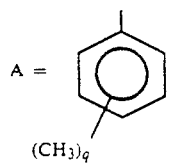

—CN, —CH=CH$_2$, Cl or Br and
q=1,2 or 3.

* * * * *